United States Patent [19]

Lyman

[11] Patent Number: 4,626,509
[45] Date of Patent: Dec. 2, 1986

[54] CULTURE MEDIA TRANSFER ASSEMBLY

[75] Inventor: George F. Lyman, Rocky Point, Me.

[73] Assignee: Data Packaging Corp., Cambridge, Mass.

[21] Appl. No.: 512,722

[22] Filed: Jul. 11, 1983

[51] Int. Cl.$^4$ .............. C12M 1/00; C12M 1/32; B01L 3/02; B67D 5/00

[52] U.S. Cl. ............................ 435/287; 435/293; 73/863.32; 73/864.11; 222/43; 222/48; 422/100

[58] Field of Search ............... 435/287, 292, 293, 294, 435/299, 300, 301; 422/100, 63, 65, 73, 102, 104; 222/309, 206, 330, 43, 48, 47, 509; 73/863.32, 364.11, 864.18; 220/21, 23.8; 141/368, 242, 243, 244, 245, 258, 259, 260, 261, 262, 152, 27, 67, 234, 237, 238

[56] References Cited

U.S. PATENT DOCUMENTS

| | | | |
|---|---|---|---|
| 2,096,461 | 10/1937 | Mane et al. | 222/382 |
| 2,769,573 | 11/1956 | Miller | 222/309 |
| 3,153,498 | 10/1964 | Bakker | 222/509 X |
| 3,568,735 | 3/1971 | Lancaster | 422/100 X |
| 3,650,306 | 3/1972 | Lancaster | 422/100 X |
| 3,807,235 | 4/1974 | Lefkovits et al. | 73/864.11 X |
| 3,837,534 | 9/1974 | Natelson | 222/309 X |
| 4,047,438 | 9/1977 | Sekine | 73/864.11 X |
| 4,106,911 | 8/1978 | Marcelli | 435/287 X |
| 4,115,200 | 9/1978 | Anderson | 435/293 |
| 4,158,035 | 6/1979 | Haase et al. | 422/100 X |
| 4,231,403 | 11/1980 | Sogi et al. | 435/287 X |
| 4,235,971 | 11/1980 | Howard et al. | 435/301 X |
| 4,444,062 | 4/1984 | Bennett et al. | 73/864.11 X |
| 4,461,328 | 7/1984 | Kenney | 141/238 X |
| 4,478,094 | 10/1984 | Solomaa et al. | 73/863.32 |
| 4,511,534 | 4/1985 | Bennett, Jr. et al. | 422/100 |

FOREIGN PATENT DOCUMENTS 2525770 10/1983 France .................. 435/294

Primary Examiner—Robert J. Warden
Assistant Examiner—Randall E. Deck
Attorney, Agent, or Firm—Wolf, Greenfield & Sacks

[57] ABSTRACT

A system for transferring liquid to a multi-well culture plate which includes a machine having a frame upon which is mounted a platform for supporting the culture plate, a transfer plate above the platform and a piston plate above the transfer plate. The transfer plate includes a plurality of chambers closed at the top by a diaphragm. The open bottoms of the chambers may be immersed in a source of the liquid to be transferred on the platform such as a culture plate or reservoir, and the piston plate may be selectively inserted into the chambers of the transfer plate against the diaphragm so that the liquid may be drawn into the chambers from the source. The liquid thereafter may be discharged from the chambers into a multi-well culture plate placed on the platform. A shuttle is mounted adjacent the platform for selectively positioning a liquid source and a culture plate in alignment with the transfer plate, and a calibrated metering control is attached to the piston plate to enable the system to measure accurately, repetitively and conveniently the liquid transferred.

7 Claims, 21 Drawing Figures

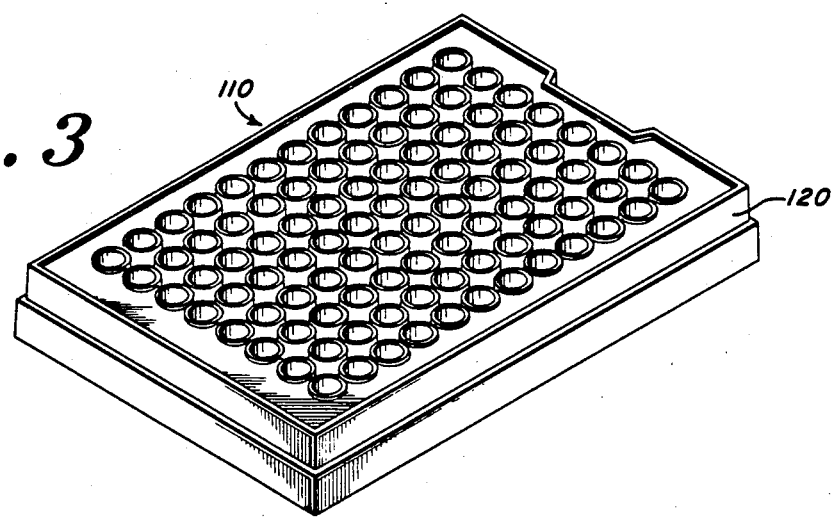
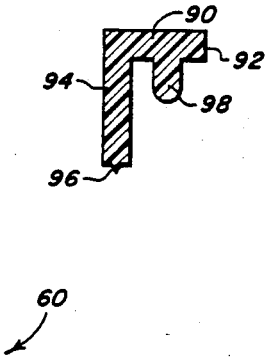
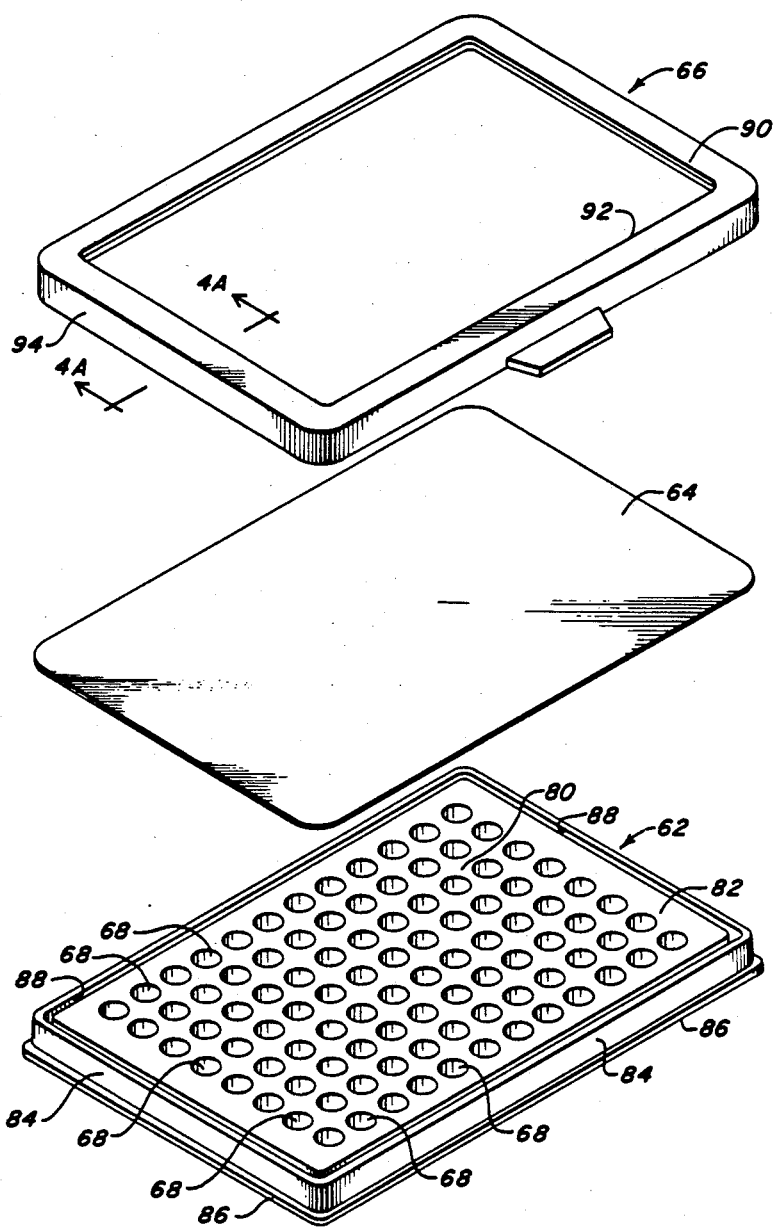

CULTURE MEDIA TRANSFER ASSEMBLY

This invention relates to equipment used in the laboratory to transfer media to a multi-well culture dish, and more particularly, is an improvement over the system shown in copending application Ser. No. 449,775 filed Dec. 14, 1982 entitled "Culture Media Transfer Assembly" having a common assignee with this application. That application inter alia discloses a machine which functions essentially as a multi-channel pipetter capable of simultaneously depositing media into a multi-well culture plate such as a 96-well tissue culture dish without cross contamination between the several wells in a single dish or between successive dishes filled by the assembly.

A typical use of the invention is to transfer cells growing in one media in a multi-well culture dish to a second multi-well dish containing fresh media so as to lessen the cell concentration in each well or to supplement the nutrients available to the growing cells. Another typical use of the assembly is to load the wells of a multi-well culture dish with fresh media. In the first example of use of the invention, cells typically growing in a 96-well tissue culture plate may be withdrawn and deposited in a second 96-well tissue culture plate whose wells contain fresh media. In the second example of use of the invention, the media may typically be drawn into the transfer plate of the assembly from a reservoir, and the media drawn into the transfer plate is then deposited in the wells of the multi-well tissue culture plate.

One important object of this invention is to provide a more convenient means for moving culture plates and media sources on the machine into and out of operative position.

Another important object of this invention is to provide an improved control over the machine so as to enable the user to measure with greater accuracy the amount of media or other liquid being transferred and to make accurate repetitive transfers.

The machine of the earlier application Ser. No. 449,775 includes a frame which has a support for a transfer plate having a plurality of chambers that receive media or other liquid from a source and that subsequently deposit it in the culture dish. Disposed beneath the support is a platform which is adapted to carry the media source as well as the multi-well culture dish into which the media or other liquid is to be deposited. The platform may be manually elevated so as to immerse a portion of the transfer plate in the media in the source container. On the frame of the machine and above the transfer plate is an array of pistons that are aligned with the several transfer plate chambers. The pistons may be manually inserted into and withdrawn from the chambers so as to draw media into the chambers from the source container when the effective size of the chambers is increased and to expel the media from the chambers into a multi-well culture dish on the platform when the effectiveness of the chambers is decreased. The pistons are moved by a cam carried on a shaft in turn rotated by a handle.

In accordance with the present invention, a shuttle is mounted on a table surrounding the platform and is movable from side to side on it. The shuttle includes a pair of frames, one on each side, which are designed to be selectively positioned beneath the transfer plate. The frames are sized to carry a media (or other liquid) source as well as a multi-well culture dish. The shuttle, which is controlled manually, may be moved from a first position wherein the media source is disposed on the platform and beneath the transfer plate so that the media may be drawn into the transfer plate chambers, to a second position wherein the multi-well culture dish is disposed on the platform and beneath the transfer plate so that the media in the chambers may be deposited in the wells.

The second improvement of the present invention relates to the metering control. The control includes a detent plate mounted on the frame of the machine adjacent the shaft which supports the cam that raises and lowers the pistons. A first disc is fixed to the shaft and carries a ball plunger which cooperates with the detent to establish a readily recognizable starting position for the shaft and the pistons. A second floating disc rotatable on the shaft with respect to the first disc also has a ball plunger which cooperates with the detent. The periphery of the second disc is calibrated and cooperates with a reference line on the first disc. To set the amount of liquid to be transferred with each operation of the machine, the operator turns the shaft with the first disc to align the reference line with the selected volume calibrated on the second disc and thereafter locks the two discs together. In that fashion, both a starting and a volume reference is established for the operator by means of the ball plungers.

These and other objects and features of the present invention will be better understood and appreciated from the following detailed description read in connection with the accompanying drawings.

BRIEF FIGURE DESCRIPTION

FIG. 3 is a perspective view of a 96 well plate which is typical of the multi-well culture dishes which may be used on the transfer machine of FIG. 1;

FIG. 4 is an exploded view of a transfer plate constructed in accordance with this invention, which may be used in combination with the machine of FIG. 1 to transfer liquid to and from a multi-well dish such as shown in FIG. 3;

FIG. 4A is a cross-sectional view of the cover of the transfer plate taken along section line 4A—4A in FIG. 4;

Figure 20:
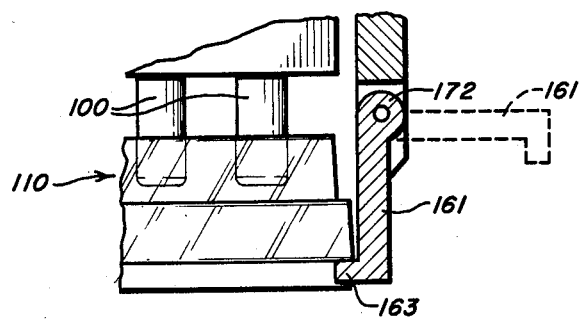
Figure 21:
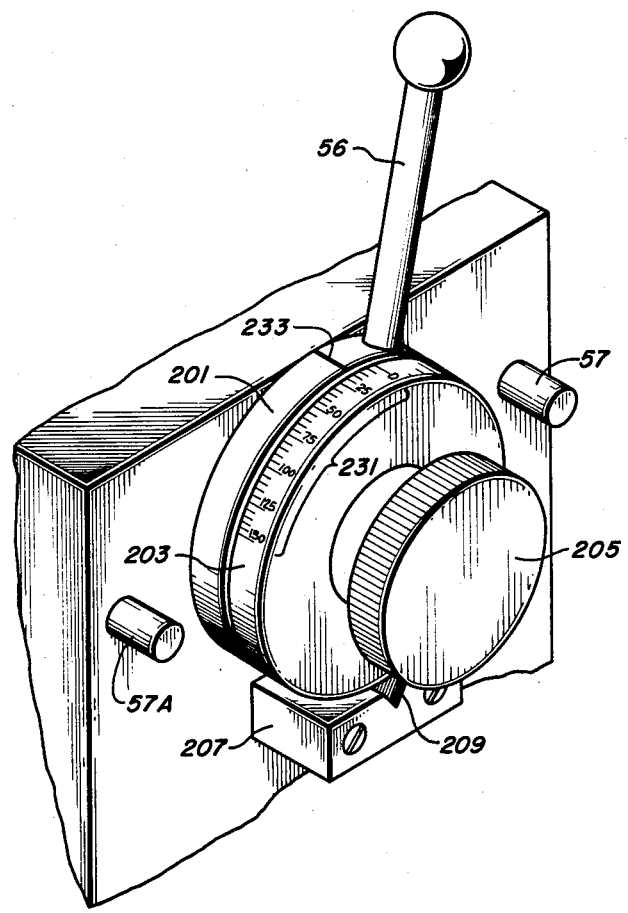

FIG. 20 is a fragmentary cross-sectional view of the machine showing a pivotally mounted door on the front which supports the front edge of the transfer plate when the door is closed and in broken lines suggesting the door in the open position to enable the transfer plate to be inserted; and FIG. 21 is a fragmentary perspective rear view of the machine showing the metering control for the piston plate.

DETAILED DESCRIPTION

The machine shown in FIGS. 1, 2, 18 and 19 is used to transfer liquid such as culture media from a source to a multi-well dish which typically may be a 96 well tissue culture plate. The source itself may be a multi-well plate or it may be a reservoir of virgin media. One common application of the machine is to dilute tissue cultures by removing cultured media from one multi-well plate and depositing the media in another multi-well plate which contains some virgin material. The machine of this invention enables the transfer to be conveniently, accurately, and inexpensively made.

The machine, which typically may be made of stainless steel or other material that may be autoclaved, includes a frame 20 that is generally U-shape in cross section (see FIG. 2) and has a rear wall 22, base 24 and top 26. The base 24 and top 26 are connected to side panels 25 and 27, respectively, that form bottom and top housings 29 and 31 in the frame. The bottom housing has a table 33 in the center of which is an elevatable platform 28 (see FIGS. 2, 18 and 19). A shuttle 35 described in greater detail below is movable on the table for selectively moving a liquid source (transferer container) and multi-well dish (transferee container) onto the platform. A piston plate 30 is mounted on top 26 for vertical movement in the top housing 31. A transfer plate retainer 32 is disposed between the platform 28 and piston plate 30 and is designed to hold the transfer plate in a fixed position in the machine.

Figure 2:
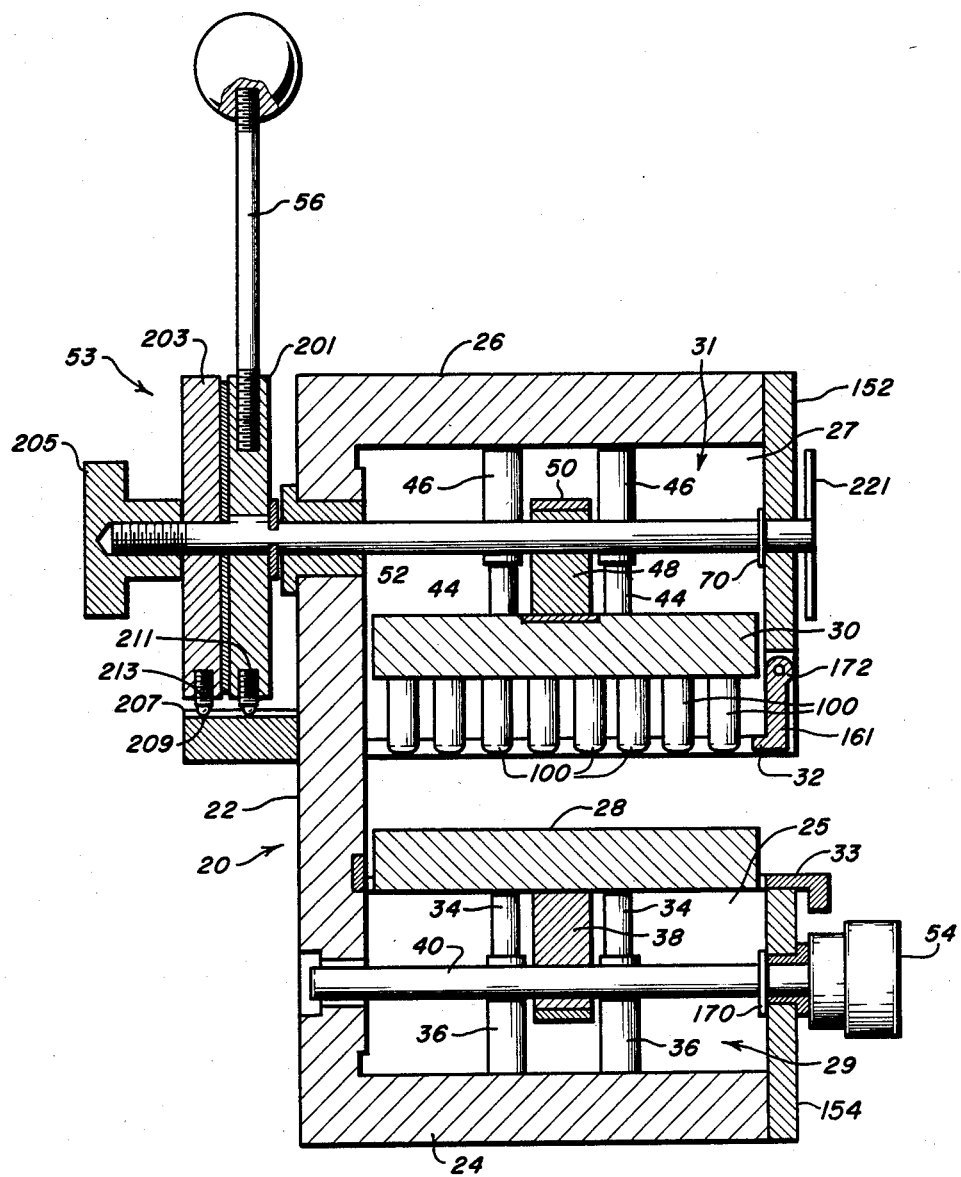
FIG. 2 is a vertical cross-sectional view of the machine taken along the section line 2—2 in FIG. 1.

As shown in FIG. 2, platform 28 is supported for vertical movement on base 24 by a plurality of pins and bushings 34 and 36, respectively, connected to the platform 28 and base 24. Actuation of the platform is accomplished by means of cam 38 (see FIGS. 18 and 19) carried on shaft 40 and captured within cage 42 attached to the platform. Handle 54 on the front of the machine rotates the shaft 40. A similar arrangement is provided to support the piston plate 30. Pins 44 and bushings 46 are respectively connected to the piston plate 30 and top 26, and a cam 48 captured within cage 50 and supported for rotation on shaft 52 raises and lowers the piston plate. A metering control 53 (see FIGS. 18 and 21) is mounted on shaft 52 to enable accurate repetitive transfer to be made by the machine. The pins, bushings, shafts, cams and cages of the platform 28 and piston plate 30 are contained within the bottom and top housings, respectively. Handle 56 is connected to shaft 52 to rotate the cam 48. The operator by means of the handles 54 and 56 may selectively move either or both the platform 28 and the piston plate 30 up or down on the frame 20.

Figure 5:
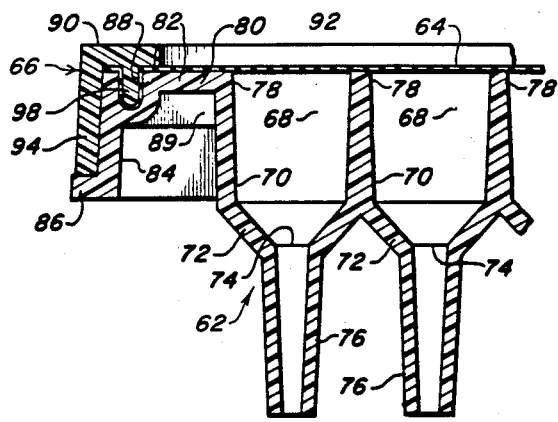
FIG. 5 is an enlarged fragmentary cross sectional view of an assembled transfer plate constructed of the parts shown in FIG. 4.
Figure 6:
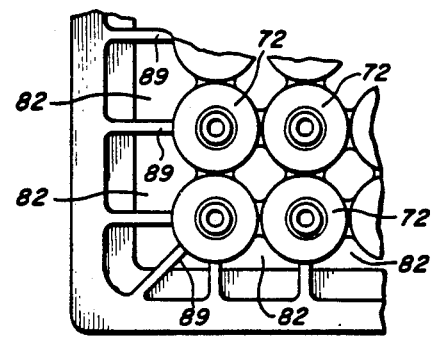
FIG. 6 is a fragmentary bottom plane view of the base of the cluster dish shown in FIGS. 4 and 5.

Before describing further details and the operation of the machine and the way it may be used in the laboratory, the transfer plate used with the machine will be described, as the functions of the machine and the transfer plate are interrelated. The transfer plate 60 shown in FIGS. 4 to 6 includes a base 62, diaphragm 64 and cover 66. Base 62, which is designed to be molded as a unitary structure of inexpensive plastic material such as high density styrene, includes an array of funnel-shaped chambers 68 arranged in eight parallel rows of twelve chambers each. The corresponding chambers in each row in turn form their own rows perpendicular to the twelve chamber rows. The cylindrical side wall 70 of each chamber 68 has a slight downward draft to facilitate stripping of the base from the molds during manufacture. The bottom wall 72 of each chamber is in the shape of an inverted cone and has a central opening 74 communicating with a downwardly converging stem 76 that serves as the intake and discharge passages for the chamber 68 above. The tops 78 of the several wells 68 are coplanar with the top panel 80 of the base. The periphery of panel 80 defines a horizontal flange 82 about the array of chambers 68, and the panel is surrounded by a downturned skirt 84 having an outwardly turned lip 86 at its bottom. Formed in the periphery of the panel 80 in flange 82 is a groove 88 whose function is described below. The base 62 is stiffened by short ribs 89 on the bottom of panel 80 (see particularly FIG. 6) that extend from the skirt 84 to the side walls 70 of the chambers.

Cover 66 of the transfer plate, which may be made of the same material as the base 62, has a top wall 90 with a large rectangular central opening 92 so that the cover has a frame-like configuration sized to overlie the flange 82 and groove 88 of the base. A rim 94 extends downwardly from the periphery of the wall 90 and is preferably provided with a bead 96 at its bottom (see FIG. 4A) which may be ultrasonically welded to the top of lip 86 of base 62 when the transfer plate is assembled. Just inwardly of rim 94 and depending downwardly from the bottom of top wall 90 of cover 66 is a tongue 98 which is sized to fit within groove 88 in panel 80 of the base. When the cover is being assembled on the base, tongue 98 automatically aligns itself with the groove 88 so that the parts may be assembled in the manner shown in FIG. 5.

Diaphragm 64 which typically may be made of latex rubber sheet material is stretchable in two directions and is cut so as to conform in the unstretched condition quite accurately to the plan of top wall 80 of base 62 so as to fully span the groove 88 about the four sides of the base. Consequently, when the diaphragm 64 is loosely laid on the top wall 80 of the base 62 and the cover 66 is applied, the tongue 98 stretches the diaphragm into the groove and holds the diaphragm firmly against the top wall 80 and close the top of each of the chambers 68. The cover and base are ultrasonically welded together along the bottom of the rim 94 and the upper surface of the lip 86 of the cover and base, respectively, at bead 96.

Figure 7:
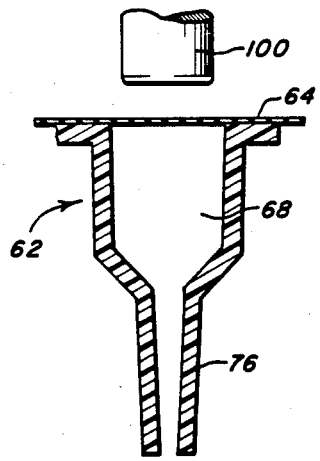
FIGS. 7–13 are diagramatic views showing the manner in which the transfer plate of FIGS. 4–6 functions to transfer liquid from one plate to another.

The manner in which the transfer plate 60 operates to remove liquid from one container and deposit it in another is diagramatically illustrated in FIGS. 7 through 13. In these figures, a single transfer plate chamber 68 is shown. In FIG. 7, base 62 with its chamber 68 and stem 76 are shown covered by diaphragm 64, and disposed above the diaphragm is a piston 100. The chamber 68 is empty, and no pressure is being exerted on the diaphragm 64 by the piston.

Figure 8:
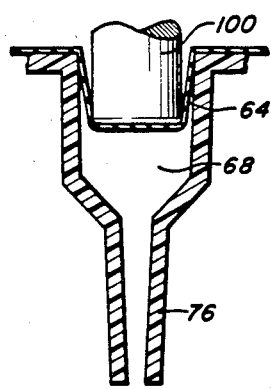

In FIG. 8 the piston 100 is shown to project into chamber 68 by stretching the diaphragm 64, so as to reduce the volume of chamber 68. The stretched diaphragm forms a seal about the top of the chamber. The next step in the process is to place the stem 76 of the chamber in the liquid 102 in the transferrer container represented by well 104. If the piston 100 is thereafter partially withdrawn from chamber 68, pressure in the chamber is reduced so as to cause the transfer plate to draw a portion of the liquid 102 into the chamber from well 104 as is suggested in FIG. 10. Piston 100 does extend, however, a short distance into the chamber 68 so as to maintain the air tight seal between the diaphragm and the edge of the top 78 of the chamber.

Figure 13:
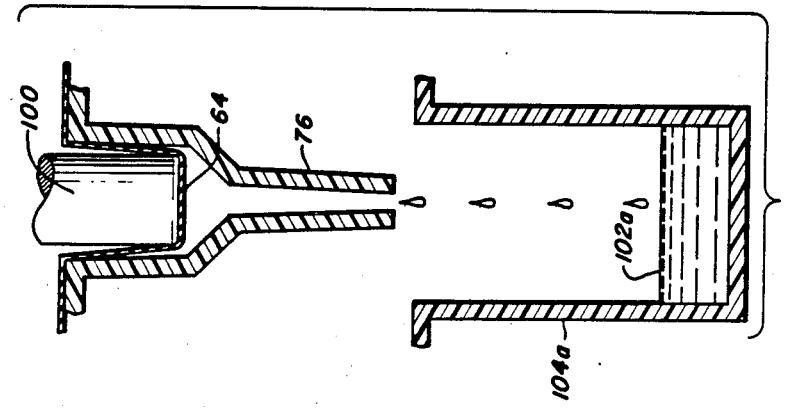
Figure 12:
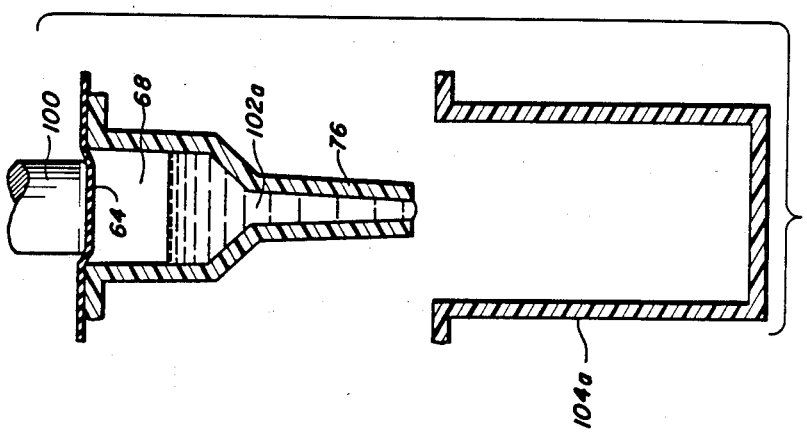
Figure 11:
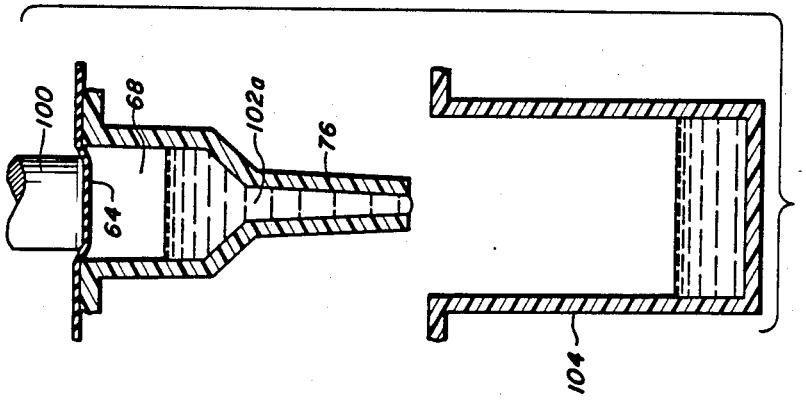
Figure 14:
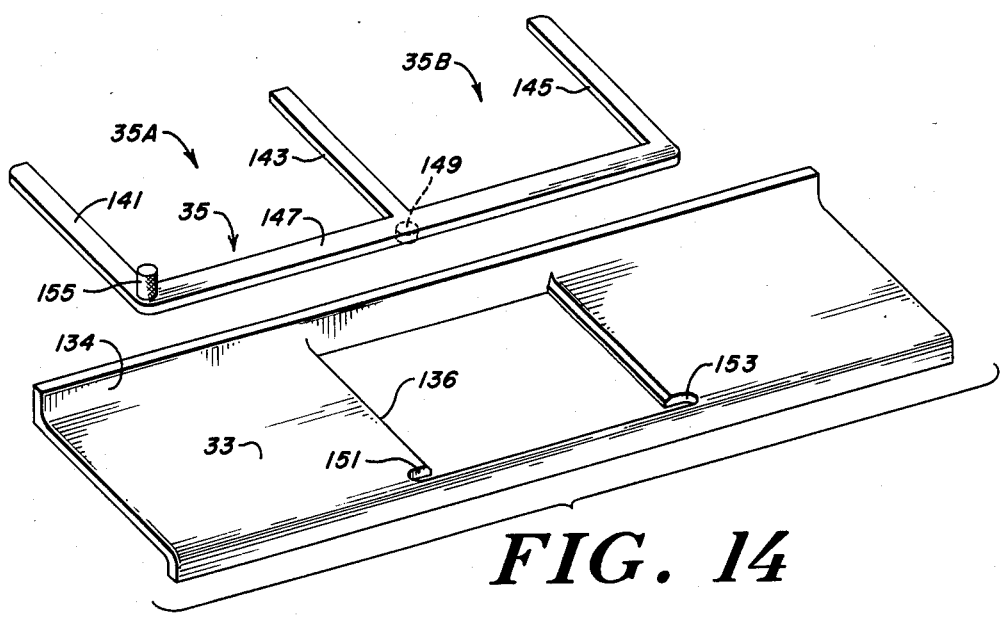
FIG. 14 is an exploded view of the table and shuttle of the machine in FIG. 1.
Figure 15:
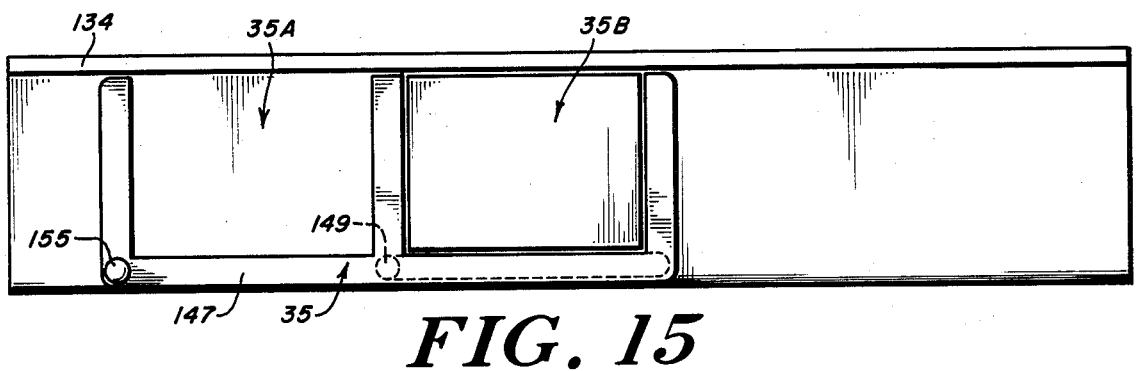
FIG. 15 is a top plan view of the shuttle mounted on the table and with the shuttle in the left position.
Figure 16:
FIG. 16 is a front elevation view of the shuttle and table of FIG. 15.
Figure 17:
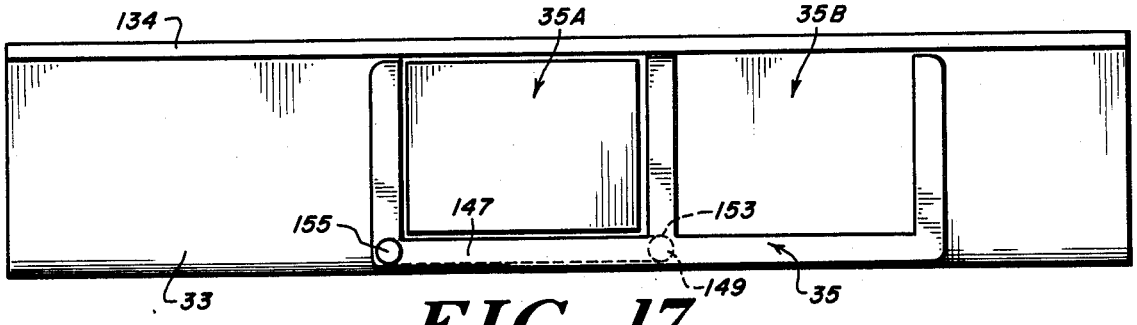
FIG. 17 is a view similar to FIG. 5 but showing the shuttle in the right position.

The partially filled chamber 68 is then removed from the liquid 102 in the well 104 as shown in FIG. 11, and the chamber 68 retains the column of fluid 102a because of the difference in pressure above and below the column. FIG. 12 suggests that a transferee container represented by well 104a is positioned beneath the transfer plate 60 to receive the liquid column 102a. The well 104a in FIG. 12 is empty. To discharge the column of liquid 102a into the well 104a, the piston 100 is rapidly driven to a lowermost position in well 68 as shown in FIG. 13. The rapid increase of pressure applied to the top of the liquid will cause the liquid to flow from the chamber 68 to well 104a as suggested.

The machine of FIGS. 1, 2, 18 and 19 is designed to cause the transfer plate 60 to perform the sequence of steps shown in FIGS. 7 to 13. And it is specially calibrated so as to allow the machine to transfer precisely measured quantities of liquid from the transferrer source to the transferee container and provide it with accurate repeatability. A typical multi-well plate which may contain the source of the liquid media and/or serve as the plate to receive the liquid is shown in FIG. 3. The configuration of that plate and others that may be used with the machine form no part of the present invention, and the plate of FIG. 3 is described only briefly. The plate 110 includes eight rows of twelve wells each formed in an array of orthogonal rows, and the plate has a surrounding rim 120 which supports the tray on a horizontal surface. The bottoms of the wells (not shown) are closed, and with the tray cover removed as in FIG. 3, the tops of the wells are open so as to afford ready access to them. The general format of the wells in the tray has been standardized by the industry so that the centers of the wells are an established distance apart and the overall tray size is determined. Typically, a cluster tray of the type shown in FIG. 3 is used to grow separate tissue cultures for experimental or test purposes. The multi-well dish provides a convenient means of keeping together a number of corrolated tests while maintaining their separation by virtue of their separate independent wells. During normal testing procedures it is frequently desired to dilute the tissue cultures, and this may be accomplished by removing a part of the contents of each well and depositing the material in another multi-well dish with additional fresh media. The machine and transfer plate of this invention is ideally suited for this operation.

In FIGS. 1, 2, 18 and 19 the machine 20 is shown to include a table 33 on base 24 screwed or otherwise secured to the side walls 25 of the base. The back of the table 33 is provided with an upstanding flange 134 to prevent articles placed on the table from sliding off the back of it.

Figure 18:
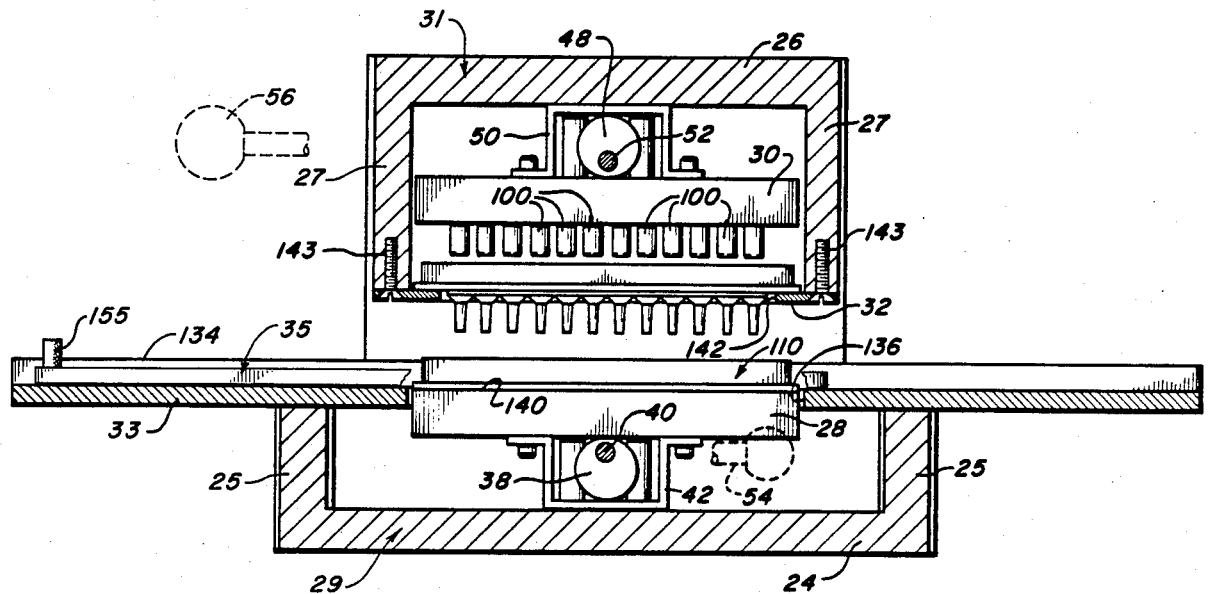
FIG. 18 is a vertical cross-sectional view of the machine taken along section line 18—18 in FIG. 2 but with the piston plate fully elevated and the platform retracted to its lower position.
Figure 19:
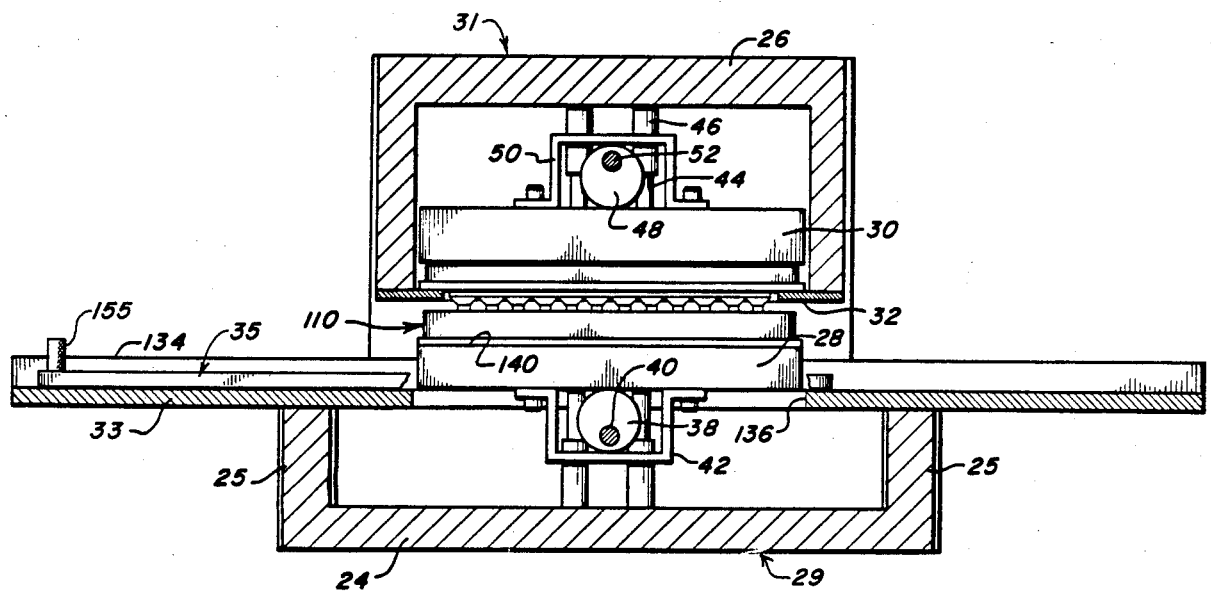
FIG. 19 is a cross-sectional elevation view similar to FIG. 18 and showing the piston plate fully lowered and the platform fully raised.

The central portion of table 33 is provided with an opening 136 through which platform 28 projects. In FIG. 18 platform 28 is shown in its lowermost position wherein its upper surface 140 is coplanar with the upper surface of table 33. In the position shown in FIG. 18, it will be appreciated that a multi-well plate may be easily slid on or off the platform from or to either side of table 33.

In FIGS. 14–17 the shuttle 35 for moving the mutli-well plates or reservoir on and off platform 28 is shown. The shuttle is generally E-shaped, having parallel arms 141, 143 and 145 perpendicular to base bar 147, and the bar and arms define two frames 35A and 35B sized to receive a multi well dish such as shown in FIG. 3 or a similarly shaped reservoir (not shown). The arms are spaced apart a distance just exceeding the width of opening 136 in table 33 so that they can straddle the opening and not interfere with the raising of platform 28 above the surface of table 33.

The bar 147 carries a downwardly extending post 149 that slides along the front of opening 136 as the shuttle moves from side to side on table 33, and the limits of movement are established by the notches 151 and 153 at the front corners of opening 136. A handle 155 is also carried by the shuttle at its left end to shift the shuttle on table 33. When the shuttle is in the left side position with post 149 in notch 151 as in FIGS. 15 and 16, the left frame 35A is exposed to the left of top housing 31, and a reservoir or cluster plate may be placed in that frame. Thereafter, by shifting the shuttle to the right as in FIG. 17, the container in frame 35A will be placed on the platform 28, and frame 35B will be exposed on the right side of top housing 31, and a multi well dish or other container may be placed in that frame. By returning the shuttle to the left, the reservoir or other container in frame 35A may be removed and the dish in frame 35B will be positioned on the platform. It will be appreciated that the shuttle will be confined to translational motion on table 33 because of the cooperation of the post 149 with the margin of opening 136 and the ends of the arms 141, 143 and 145 with the flange 134.

In FIG. 18, the transfer plate retainer 32 is shown to carry a fully assembled transfer plate 60. The retainer 32 has a central opening 142 which is somewhat smaller than the plan dimensions of the transfer plate but which is sufficiently large to allow all of the stems 76 of the individual chambers 68 to extend below the retainer.

Figure 1:
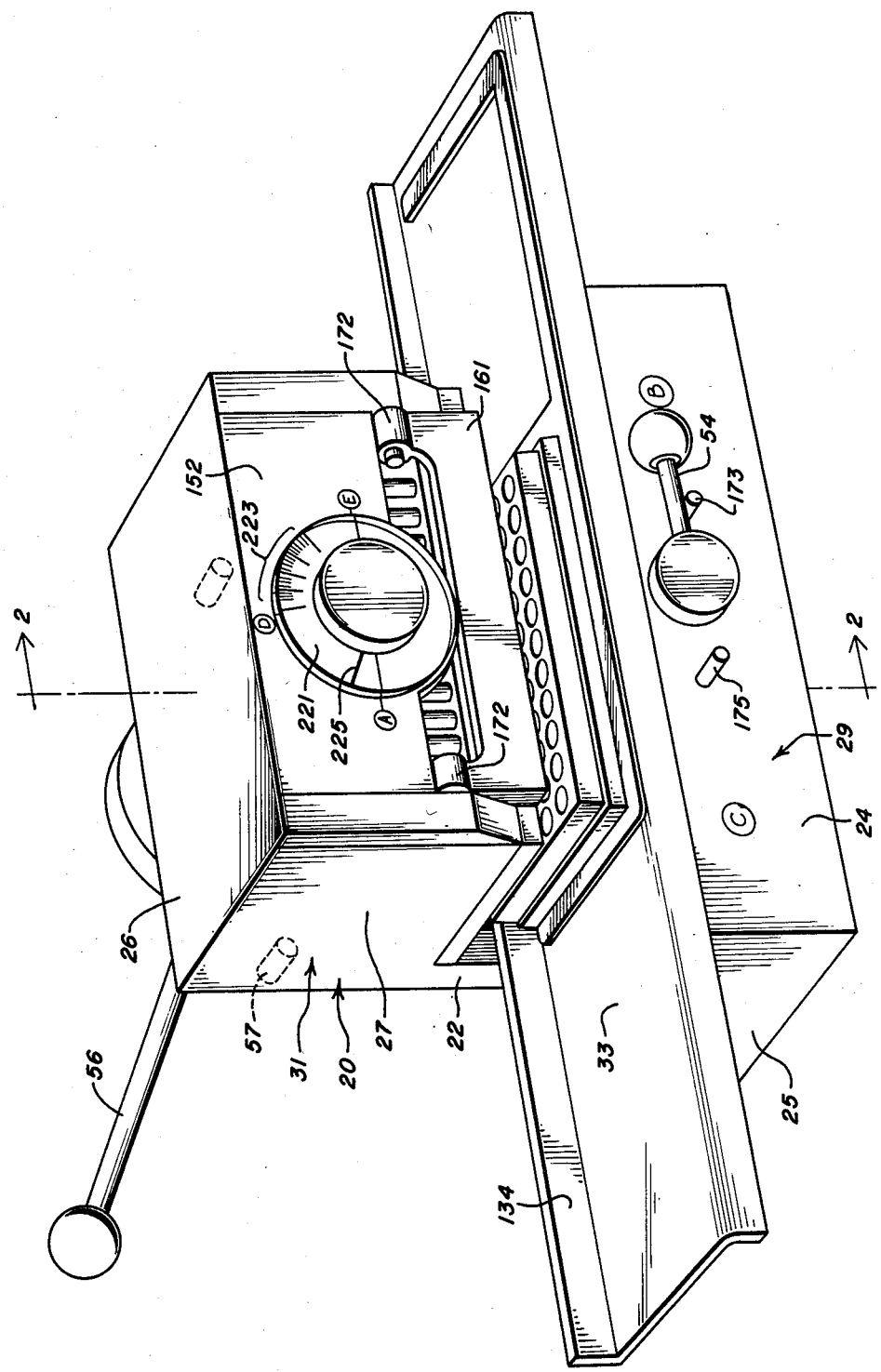
FIG. 1 is a perspective view of a media transfer machine constructed in accordance with this invention.

A door 161 having a lip 163 is shown in FIGS. 1, 2 and 20 to be pivoted on the bottom of front wall 152 of the top housing 31 by hinges 172. The door 161 is swung to the position shown in dotted lines in FIG. 20 when the transfer plate 60 is to be placed on or removed from the plate retainer 32, and the door is closed as shown in full lines in FIG. 20 when the plate 60 is in place so as to support the front edge of the plate. Thus, the plate is supported along the sides and back by the retainer 32 which is screwed to the top housing 31 by the screws 143 and along the front by the lip 163 on door 161. This support prevents the transfer plate from bowing downwardly under the considerable force imposed by the pistons 100 when pressed into the diaphragm 64. It will be appreciated that if the plate 60 deflects under the force of the pistons, the chambers at the center of the transfer plate will not draw in or dispense the same volume of liquid as the chambers at the ends of the plate, as the effective lengths of the strokes of the pistons in the chambers will not be uniform. Such variations will produce inaccuracies in test results which may not be acceptable.

In the embodiment of the transfer machine illustrated the transfer plate does not move up or down in the machine but rather is held in fixed position, and the piston plate 30 and platform 28 move to and from it. As described above, the machine screws 143 mount the transfer plate retainer 32 on the side panels 27 in the upper portion of the main frame.

Piston plate 30 is provided with a plurality of pistons 100 that correspond in format and number to the chambers 68 in the transfer plate and the wells in the transferrer and transferee multi-well plates to be serviced. As suggested above, a standard number for such multi-well dishes is 96 wells, and the machine and transfer plate shown are respectively provided with 96 pistons 100 and 96 chambers 68. As is explained below, the machine, merely by using a transfer plate with fewer chambers or by providing a transferrer container that does not register with selected ones of the transfer plate stems 76, can be used to transfer media to fewer than 96 wells.

In FIGS. 1 and 18 handle 54 is shown in the right side position as defined by contact with a stop 173 wherein the cam 38 forces the platform 28 to its lowermost position on the frame so that the upper surface 140 of the platform is coplanar with the surface of table 33. The cage 42 about cam 38 ensures that the platform 28 follows the cam, and, therefore, with the handle 54 in the position suggested in FIG. 18, the platform 28 necessarily occupies its lowermost position. Similarly, handle 56 in FIG. 18 is shown in the left position, wherein cam 48 elevates the piston plate 30 to its maximum height. Again, cage 50 ensures that the piston plate 30 follows the cam 48 to the position dictated by the handle.

In FIGS. 2 and 21, the metering control which enables the machine to accurately and repetitively dispense selected quantities of liquid is shown. It is evident that the quantity of liquid dispensed by each chamber of the transfer plate is a function of the throw or length of travel of the piston plate 30. In order for the machine to be capable of precisely repeating the dispensing function so as to be able to duplicate its actions with a series of multi-well plates, the user must have a precise indication of selected positions of the piston plate. These functions are performed by the metering control.

In FIG. 2, shaft 52 which controls the piston plate 100 is shown to carry at its rear end a pair of discs 201 and 203. Disc 201 which carries handle 56 is keyed to and rotates with the shaft 52 while disc 203 is rotatable with respect to the shaft. At least one of the adjacent faces of the discs 201 and 203 carries a cork or similar material that serves as a clutch to lock the discs together when the disc 203 is tightened against disc 201 by the knob 205 threaded onto the rear end of shaft 52.

A block 207 is mounted on rear wall 22 beneath the discs 201 and 203 and has detent means including an upwardly open V-shaped detent or groove 209 that cooperates with the ball plungers 211 and 213 carried by the discs 201 and 203, respectively. The ball plungers and detent provide readily sensed click stops for the metering control to establish starting and measured volume positions for the shaft.

The front end of shaft 52 carries a transparent disc 221 through which volume calibrations 223 on the front wall 152 of the top housing 31 may be viewed. The disc 221 carries an index line 225 which cooperates with the calibrations 223. This metering facility on the front of the machine is used principally for course measurements of volume when precise and/or repetitive measurements are not required.

Accurate and repetitive measurements are made by the metering control 53 through the calibrations 231 provided on the periphery of floating disc 203 on the back of the machine and the index line 233 on the disc 201. As is explained in greater detail below in connection with the operation of the machine, with the handle 56 turned so that the ball plunger 211 of the disc 201 registers with detent 209, the knob 205 is loosened to allow the floating disc 203 to rotate on shaft 52 with respect to disc 201. Disc 203 is then turned to seat its ball plunger 213 in detent 209. Next, handle 56 is turned to align index line 233 with the selected volume on the calibrations 231 in FIG. 21) and the knob is tightened. With this simple procedure, the metering control establishes click stops for the zero and selected volume measurement so that the volume may be repeatedly dispensed by the machine.

The machine operates as follows:

The operator places lower handle 54 in the position shown in FIGS. 1 and 18 so that the handle lies against the stop 173. In this position, the platform 28 is in its lowermost position. Upper handle 56 is moved to the position shown in FIG. 18 so that it bears against the stop 57. In that position, the piston plate 30 is elevated to its maximum height and the index line 225 points to reference A on the front wall of the machine. With the handles 54 and 56 in the positions described, the operator may open the door 161 and slide a transfer plate 60 onto the support 32. The door 161 is then closed so as to assume the full line position of FIG. 20 in order to have its lip 163 engage the bottom edge of the plate 60 and prevent it from bowing. The shuttle 35 is moved to the left position shown in FIG. 15 and the operator places a transferrer container (either a metering reservoir or multi-well plate) in the frame 35A.

If the metering control is to be used, the operator next moves handle 56 from the position shown in FIG. 18 to the position wherein the index line 225 on the front of the machine points to position D on the frame. This position causes the ball plunger 211 to engage the detent 209 in block 207. In that position, the pistons 100 slightly deflect the diaphragm 64 of the transfer plate so as to seal the tops of the chambers 68 in the manner shown in FIG. 10. (The chambers do not, however, at this time extend into the transferrer plate as in FIG. 10.) The operator next loosens knob 205 so as to allow the floating disc 203 to turn freely on shaft 52, and the ball plunger 213 is brought into registration with detent 209. At that time, both discs 201 and 203 are in the position shown in FIG. 2. The operator next turns handle 56 so as to bring the reference line 233 into alignment with the particular volume on the calibrations 231 of floating disc 203, representing the volume to be drawn into each chamber 68 of transfer plate 60. Knob 205 is then tightened so that it no longer floats freely on shaft 52 but rather turns with it by virtue of the engagement of the clutch faces (facing surfaces of the discs 201 and 203). In this position, the pistons 100 are in the position represented in FIG. 9, but the stems are not in the transferrer container. With the metering control so set, the filling and transferring of the liquid by the machine may be conducted accurately with the detents providing click stops to establish maximum control and repeatability.

Figure 9:
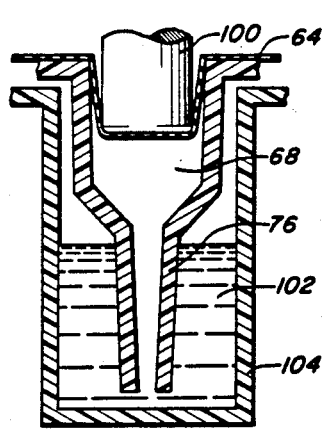
Figure 10:
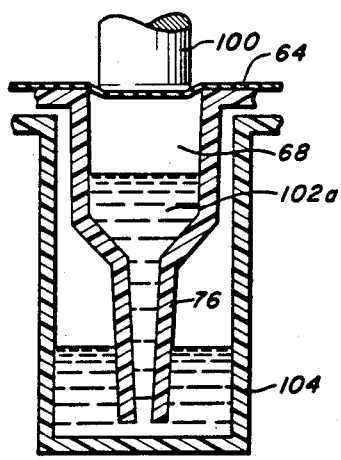

With the machine set as described, the operator moves the shuttle 35 to the right by means of handle 155 so as to bring the transferrer container in frame 35A into position on the platform 28. Next, the platform 28 is elevated by moving the handle from the position shown in FIGS. 1 and 18 to the position shown in FIG. 19 wherein the handle lies against stop 175 and the stem 76 of the transfer plate lies within the reservoir submerged in the liquid. This arrangement is shown in FIG. 9, and is established by the registration of ball plunger 213 in detent 209. With the piston plate, transfer plate and transferrer container in the position shown in FIG. 9, the operator turns handle 56 back to the start position represented by the click stop established by the ball plunger 211 carried on disc 201. This causes the transfer plate to draw liquid from the reservoir into chamber 68 as shown in FIG. 10. With the liquid in the transfer plate, the platform 28 is lowered so as to place its surface in alignment with the surface of table 33. At this time the operator may place the transferee container in the frame 35B of shuttle 35. This may have been done any time the shuttle was in the position of FIG. 17 with frame 35B exposed. With the transferee container in the shuttle, the shuttle is moved to the left position shown in FIG. 15 so as to align the several wells of the transferee container with the stems 76 of the several chambers 68 in the transfer plate. To discharge the contents of the transfer plate into the transferee container, the operator moves the handle 56 to the right position wherein the index line 225 points to position E on the face of the machine. Handle 56 will also engage stop 57A. This action causes the piston 100 to project fully into the chambers 68, and the contents of the chambers are discharged into the wells of the transferee plate 104a. In FIG. 12, the transferee plate is shown in position beneath the transfer plate, and in FIG. 13 the transferee container is shown receiving the liquid from the transfer plate. Before depositing the contents of the transfer plate into the transferee container 104a, the operator may elect to elevate the transferee container on platform 28 to move it closer to the bottoms of the stems 76. This is normally done if other matter is in the transferee container which may splash out. The operator may also test the alignment of the transferee container with the stems by temporarily elevating the transferee container by means of handle 54.

The procedure described above may be repeated by returning the handle 56 to the volume metering position established by the ball plunger 213 on disc 203 and by moving the shuttle to the right so as to once again place the reservoir on platform 28. The platform is then raised to immerse the stems 76 of the chambers 68 in the liquid reservoir. The handle 56 is then turned to the first click stop or start position established by ball plunger 211 to repeat the functions represented in FIGS. 9 and 10. Thereafter the contents are discharged into the new transferee plate.

From the foregoing description it will be appreciated that the machine is completely isolated from the media by diaphragm 64 of the transfer plate and consequently the machine may be used to perform a series of transfers without cleaning. Successive transfers may be carried out without any cross contamination merely by changing the transfer plate which is disposable. It will also be appreciated that the machine forms the individual air tight seals across the tops of the transfer plate chambers, and in assembling the transfer plate, the diaphragm is placed losely over the transfer plate base 62 and it is stretched and held in place about the diaphragm periphery as the tongue 98 enters groove 88. The transfer plate is inexpensively assembled merely by ultrasonically welding the base and cover together at the welding bead 96 on the cover at the bottom of its surrounding rim 94. Once the cover 66 and base 62 of the transfer plate are welded together, the diaphragm 64 is held in place across the top of base 62 although the seals are not formed at the tops of the individual chambers 68 until the pistons 100 force the diaphragm at least slightly into the chambers. It is unnecessary to preseal the diaphragm 64 over each chamber.

It will be apparent that the machine can be used either to transfer media from one plate to another or to transfer fresh media from a reservoir to a series of multi-well plates. When fresh media is to be transferred from a reservoir into a number of plates, the transfer plate need not be replaced, but rather may be used over and over again to supply the media to the multi-well plates. With the aid of the metering control, the successive transfers may be accurate and constant.

In some procedures where 96 well plates are used, only the inner sixty wells are utilized. This is done because the inner wells are more thermally constant and the ventilation is more even as the plates are moved from one environment to another. When it is desired to utilize only the sixty inner wells, the reservoir used may be of a size just exceeding the plan dimensions of the inner sixty wells of the tranfer plate. In such cases, it may be more convenient to remove the shuttle 35 which merely lifts off table 33 and place the reservoir manually on platform 28. When the transfer plate is lowered so that its stems extend into the reservoir, only the inner sixty stems are positioned within the reservoir and the outer 36 stems are beyond the reservoir periphery. While any form of reservoir may be used, preferably the reservoir is in the form of a shallow dish having baffles inside to prevent the media from sloshing as the reservoir is slid on and off the platform either manually or by shuttle 35. Passages should be provided through or around the baffles so as to assure that the level of media throughout the reservoir is uniform.

It will also be appreciated that with the use of the transfer machine of this invention, since each piston-diaphragm-chamber member acts independently of the others, media is only transferred from wells containing media, and empty wells do not effect the operation of the device. This is a distinct advantage over systems which generate a single vacuum over all the wells to remove media from a multi-well plate. In such systems if one or more wells is empty, the system cannot operate because the vacuum will be relieved through the stems which are not submerged in media.

Another advantage of the present invention is the ease with which it may be disassembled so that the parts can be autoclaved. To disassemble the machine, the upper and lower front plates 152 and 154 are removed by removing the screws (not shown) that hold them to the side panels 25 and 27.

While the foregoing description has stressed the application of the machine with 96 well plates, it should be appreciated that by changing the piston plate and the format of the transfer plate, the machine may be used with a variety of different well plates. While 96 well plates are by far the most widely used format, 6, 12, 24 and 48 well plates are also frequently used, and these may be accommodated in the machine of this invention by appropriately selecting the piston plate configuration.

An important advantage of this invention is that only the transfer plate has contact with the media, and the transfer plate is designed as a disposable unit. Also important is the fact that each of the 96 chambers of the transfer plate is independent of the actions of the other chambers in the transfer plate, and consequently, it is possible to transfer with any number of wells full or empty. And in addition, with this invention the volume transfers are made accurately and quickly, over and over again.

Having described this invention in detail those skilled in the art will appreciate that numerous modifications may be made of this invention without departing from its spirit. Therefore, it is not intended to limit the breadth of this invention to the embodiments illustrated and described. Rather, the scope of this invention is to be determined by the appended claims and their equilavents.

What is claimed is:

1. In a machine for transferring liquid to a multi-well culture plate having a frame, a support on the frame for a multi-chamber transfer plate which receives the liquid from a source and deposits it in the culture plate, a piston plate having an array of pistons for entering the chambers to draw liquid into and discharge liquid from the chambers, said piston plate and transfer plate being movable with respect to the culture plate, and guide means on the frame for establishing the path of travel of the piston plate; wherein the improvement comprises said guide means for controlling the movement of the piston plate comprising:
   a rotatable shaft on the frame,
   a cam on the shaft operatively connected to the piston plate causing the piston plate to follow the cam surface as the cam rotates with the shaft,
   a handle operatively secured to the shaft for rotating the shaft on the frame to in turn rotate the cam,
   first detent means on the frame adjacent the shaft,
   second detent means on the shaft for engaging the first detent means to establish a first reference position for the shaft which represents a starting position for the piston plate with respect to the transfer plate wherein the pistons enter the chambers a limited extent,
   third detent means movable on the shaft for engaging the first detent means, for establishing a second reference position for the shaft which represents a volume measurement position for the piston plate with respect to the transfer plate wherein the pistons enter the chambers a greater extent than the first position,
   and means for varying the postion of the third detent means with respect to the shaft for changing the volume measurement postion for the piston plate.

2. The machine of claim 1 wherein
said second and third detent means include discs mounted on the shaft, and said means for varying the position of the third detent includes a clutch means for locking the discs together.

3. The machine of claim 1 further comprising
first stop means positioned on the frame for engaging the handle to designate a maximum elevation position wherein the piston plate and transfer plate are further apart than the first reference position and second stop means positioned on the frame for engaging the handle to designate a minimum elevation position wherein the piston plate and transfer plate are closer together than the second reference position.

4. The machine of claim 2 further comprising
first stop means positioned on the frame for engaging the handle to designate a maximum elevation position wherein the piston plate and transfer plate are further apart than the first reference position and second stop means positioned on the frame for engaging the handle to designate a minimum elevation position wherein the piston plate and transfer plate are closer together than the second reference position.

5. An apparatus for moving a piston plate mounted on a frame between a first reference position and a second reference position, said apparatus comprising:
   a piston plate mounted on a frame;
   a rotatable shaft extending horizontally through the frame;
   means for rotating the shaft;
   a cam on the shaft operatively connected to the piston plate causing the piston plate to follow the cam surface as the cam rotates with the shaft;
   a first disc mounted on the shaft and having first detent means on its periphery;
   a second disc rotatably mounted on the shaft and having second detent means on its periphery;
   clutch means for releasably engaging the second disc to the shaft so that when said clutch means is disengaged the first and second discs can be rotated with respect to one another in order to establish a relative displacement between said first and second detent means, and when clutch means is engaged said relative displacement is fixed;
   and third detent means mounted on the frame for engaging either the first or second detent means, wherein, with said clutch means engaged to fix a relative displacement between said first and second detent means, by rotating the shaft the piston plate can be moved from a first reference position where one of said first and second detent means is positioned in the third detent means to a second reference position where the other of said first and second detent means is positioned in the third detent means.

6. The apparatus of claim 5 wherein said clutch means comprises a layer of cork disposed between the facing surfaces of said first and second discs and means for releasably compressing together said first and second discs.

7. The apparatus of claim 6 further comprising calibration lines disposed on the first and second discs for indicating the relative displacement between said first and second detent means.

* * * * *